United States Patent [19]

Baker et al.

[11] Patent Number: 5,692,518
[45] Date of Patent: Dec. 2, 1997

[54] SKIN TEST APPLICATOR

[75] Inventors: John F. Baker, Pleasant Hill; David J. Thorson, Oakland, both of Calif.

[73] Assignee: Rachman Scientific, Inc., Concord, Calif.

[21] Appl. No.: 251,729

[22] Filed: Jul. 8, 1994

Related U.S. Application Data

[63] Continuation-in-part of Ser. No. 86,929, Jul. 2, 1993, abandoned.

[51] Int. Cl.⁶ .................................................. A61B 5/00
[52] U.S. Cl. .................................................. 128/743
[58] Field of Search ........................ 128/743; 604/46, 604/47, 191, 280, 283; 606/181–183, 185, 186

[56] References Cited

U.S. PATENT DOCUMENTS

| | | |
|---|---|---|
| 1,405,976 | 2/1922 | Dhooge . |
| 1,904,061 | 4/1933 | Larson . |
| 2,522,309 | 9/1950 | Simon . |
| 2,732,249 | 1/1956 | Siracusa . |
| 3,289,670 | 12/1966 | Krug et al. . |
| 3,556,080 | 1/1971 | Hein . |
| 4,237,906 | 12/1980 | Havstad et al. ............... 128/743 |
| 4,304,241 | 12/1981 | Brennan ....................... 128/743 |
| 4,711,247 | 12/1987 | Fishman ....................... 128/743 |
| 4,878,900 | 11/1989 | Sundt ........................... 604/119 |

*Primary Examiner*—Max Hindenburg
*Attorney, Agent, or Firm*—Donald L. Beeson

[57] ABSTRACT

A skin test applicator has a applicator handle (21) and separately storable test elements (13). A complimentary snap-fit attachment structure (33, 43) is provided on the applicator handle and test elements to permit the applicator handle to operatively pick up and releasably hold one or more test elements from a suitable sterile storage tray. In one version of the invention, pressure heads (15) are arranged in staggered relation on the test elements to provide maximum spacing between test heads. The skin test applicator reduces storage requirements and the amount of refuse that must be discarded immediately following the administration of a skin test for the diagnosis of an allergic response or other diagnostic test.

13 Claims, 7 Drawing Sheets

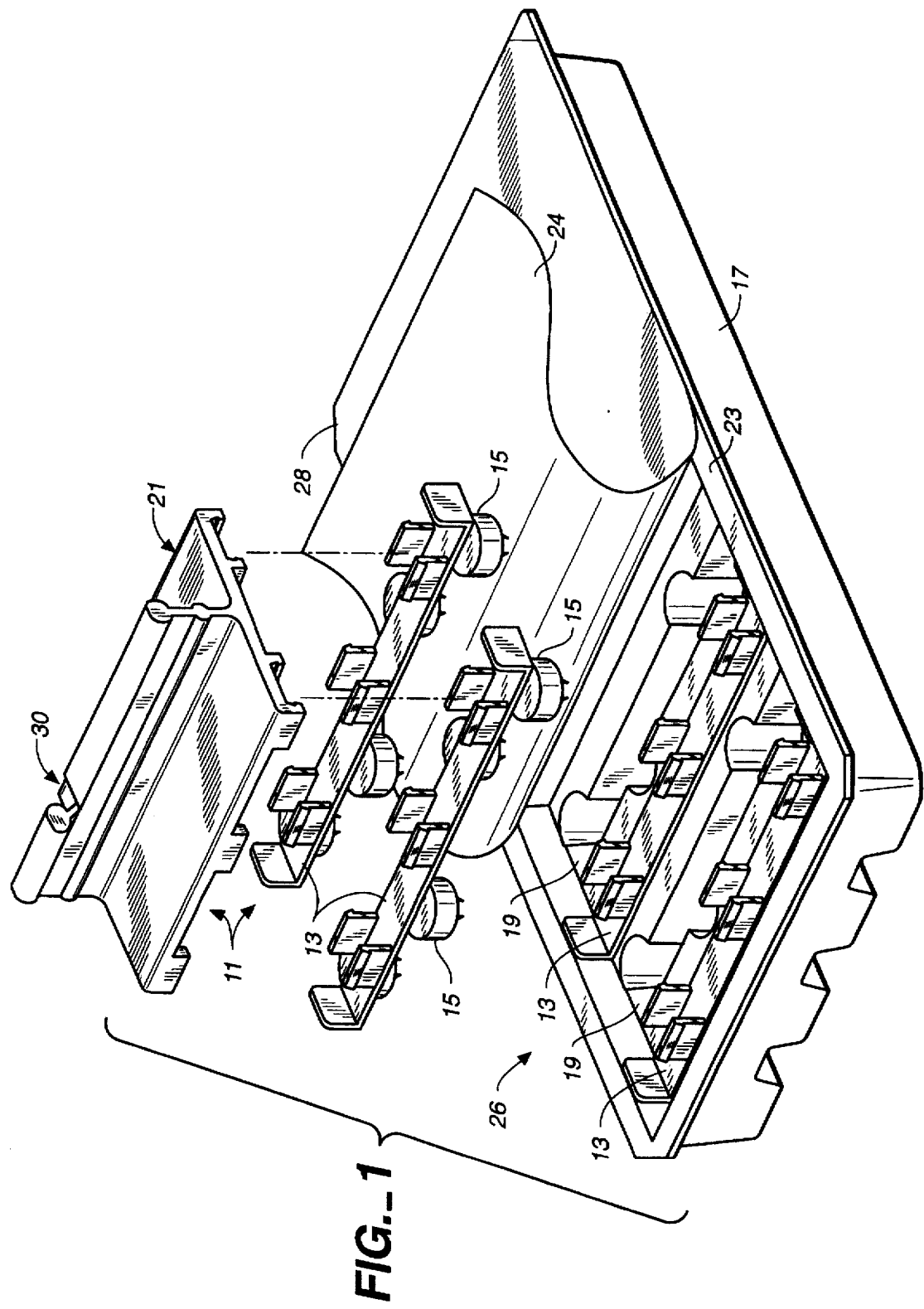
FIG._1

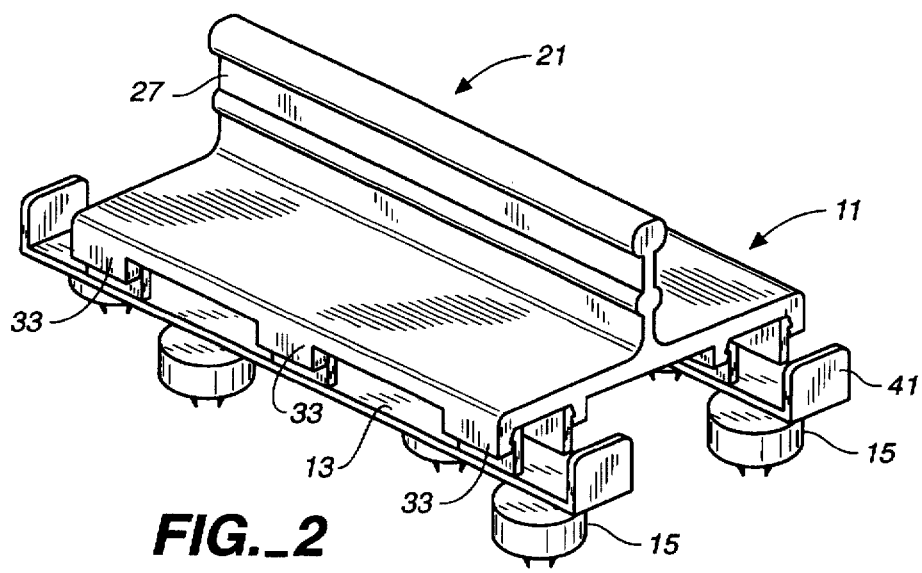
FIG._2
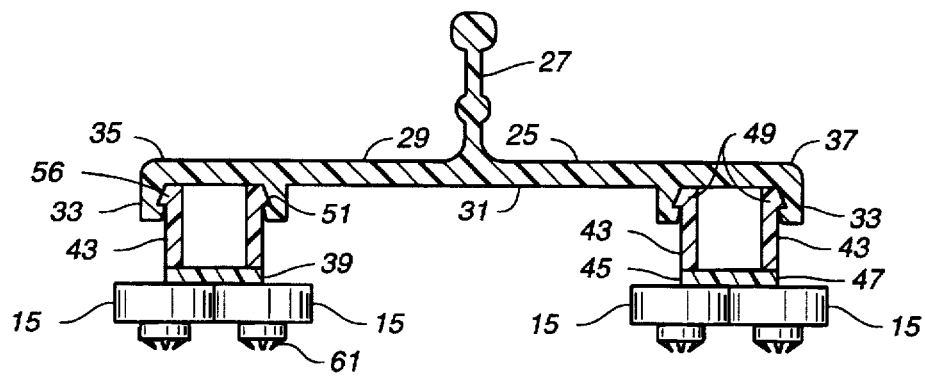
FIG._3
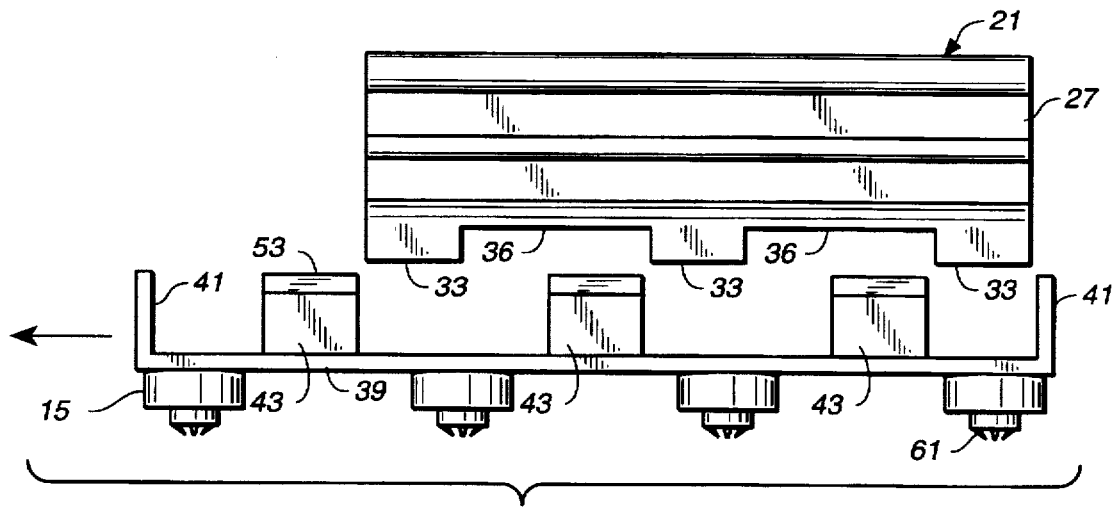
FIG._4

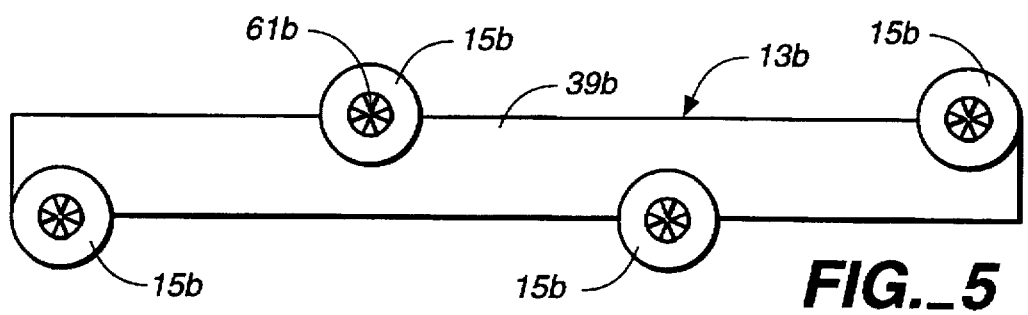
FIG._5
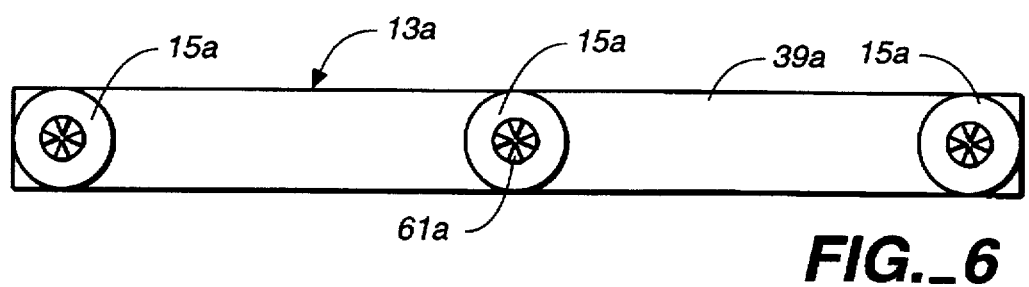
FIG._6
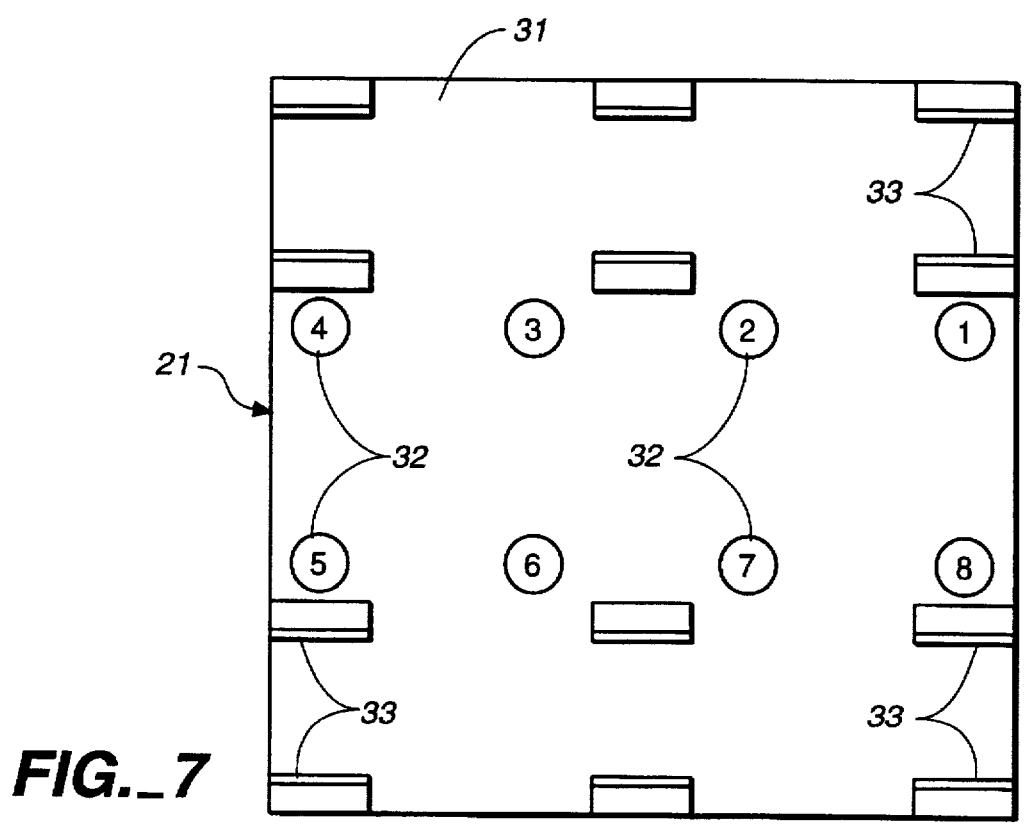
FIG._7

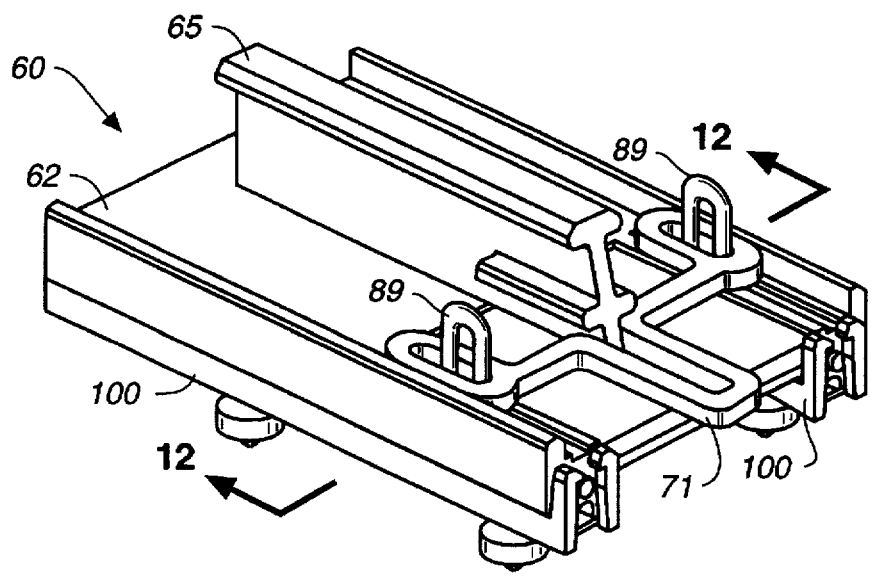
FIG._8
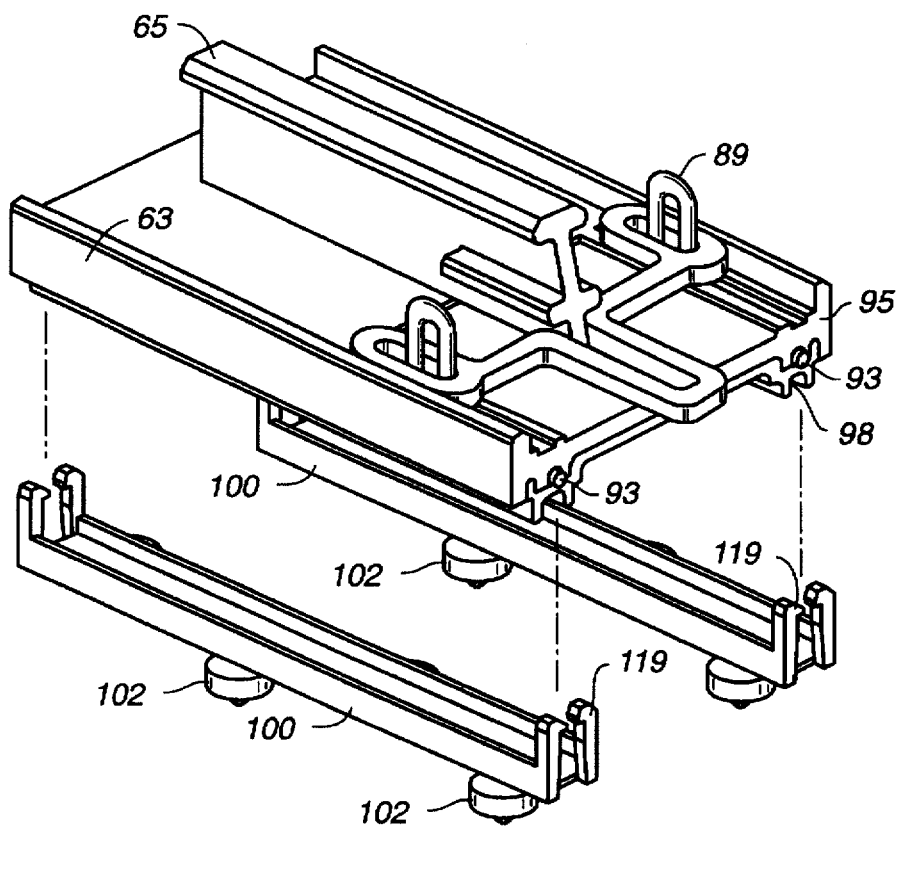
FIG._9

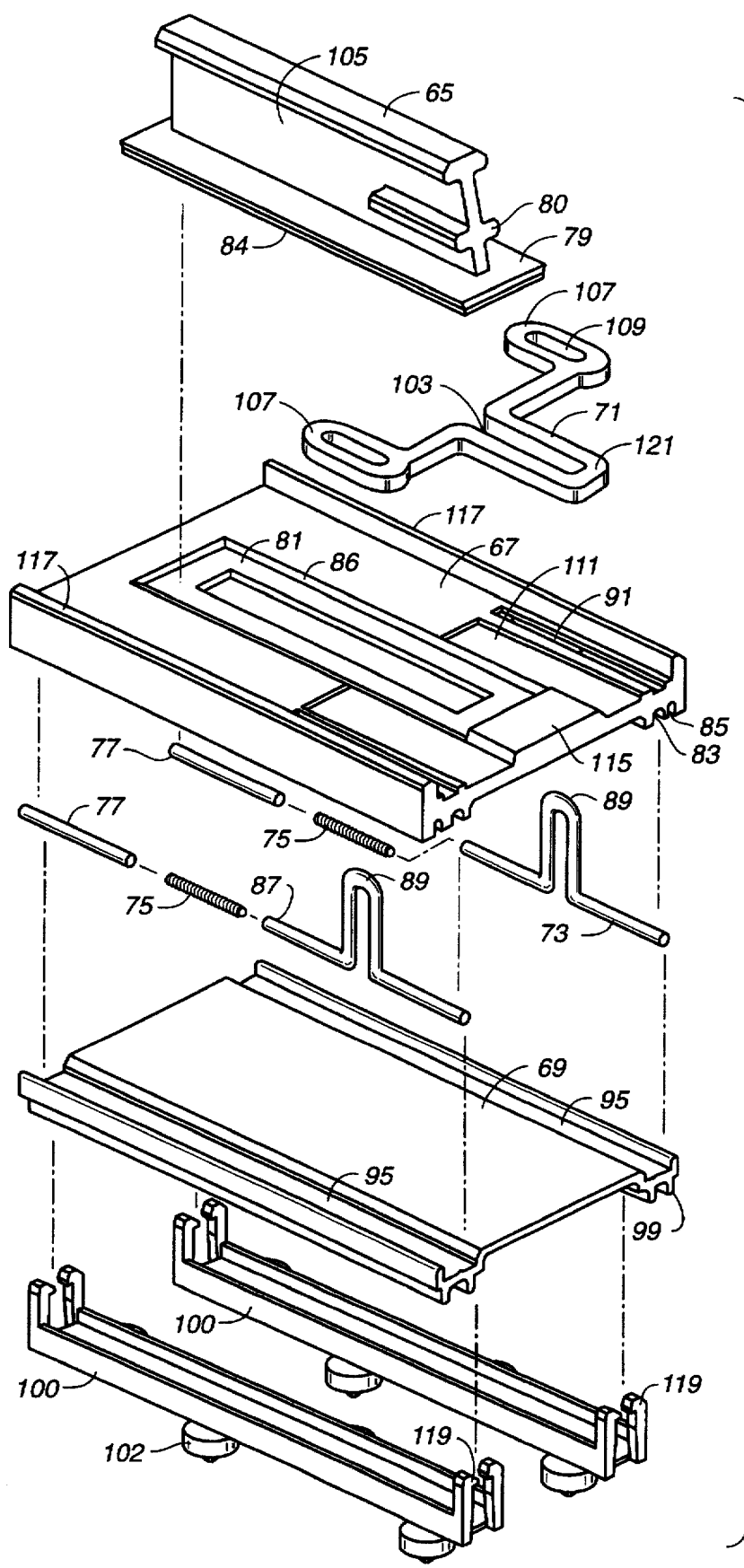
FIG._10

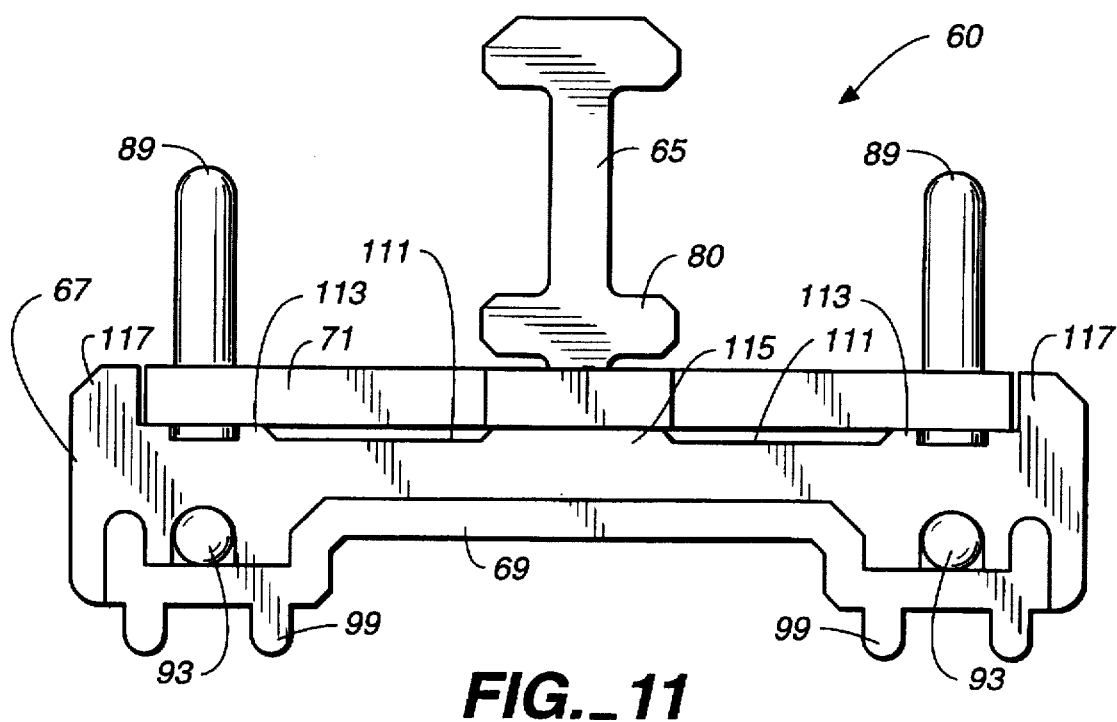
FIG._11
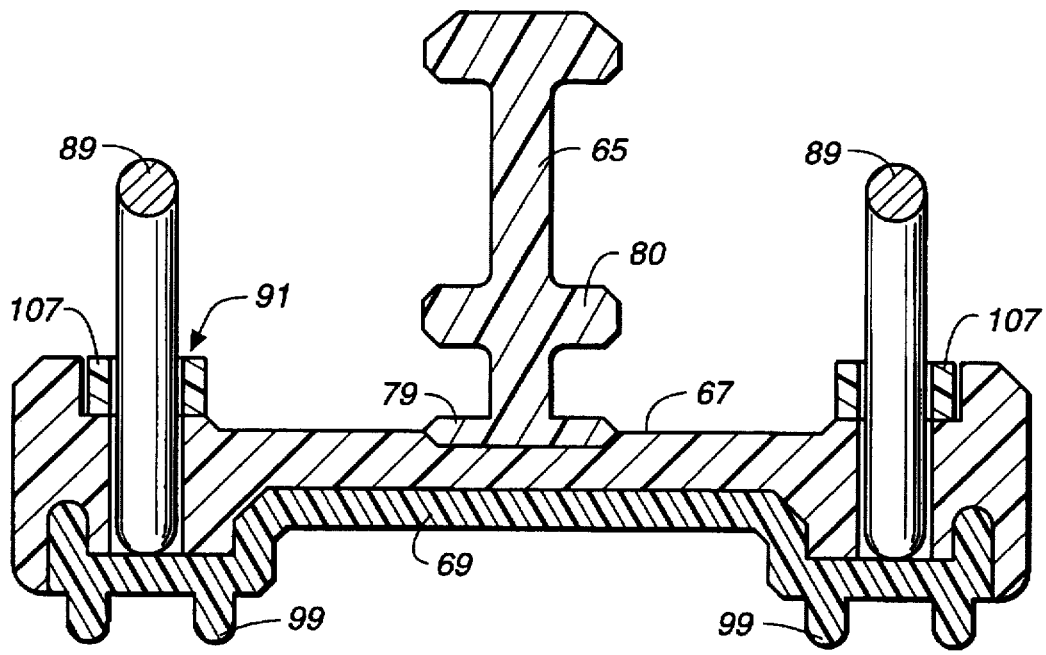
FIG._12

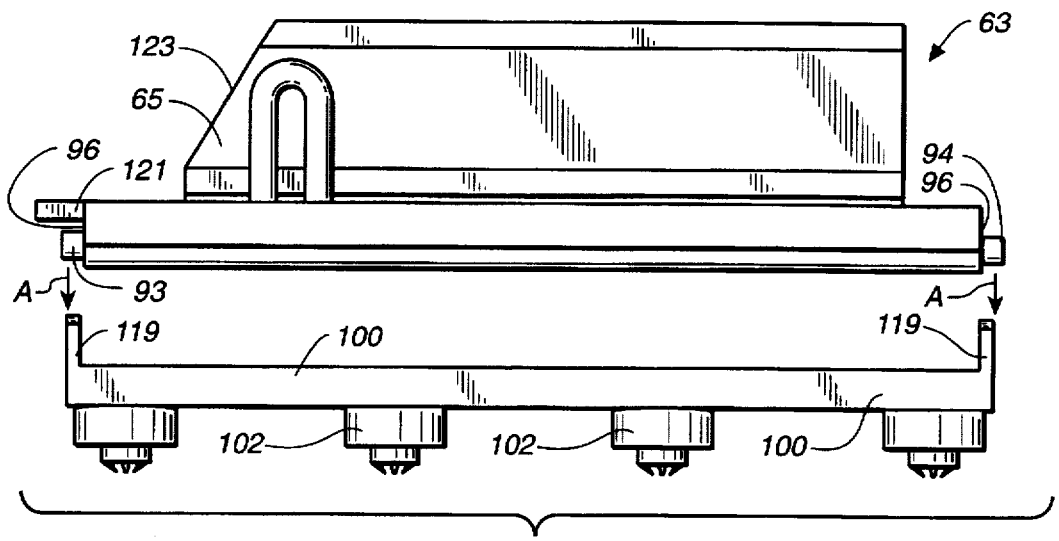
FIG._13
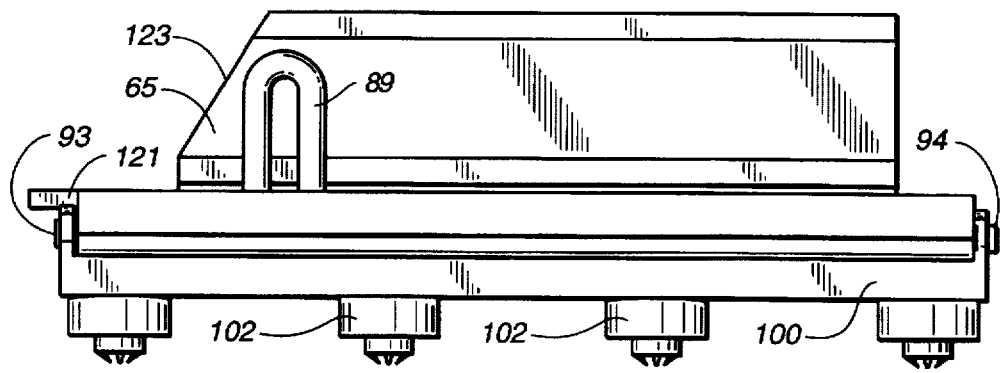
FIG._14
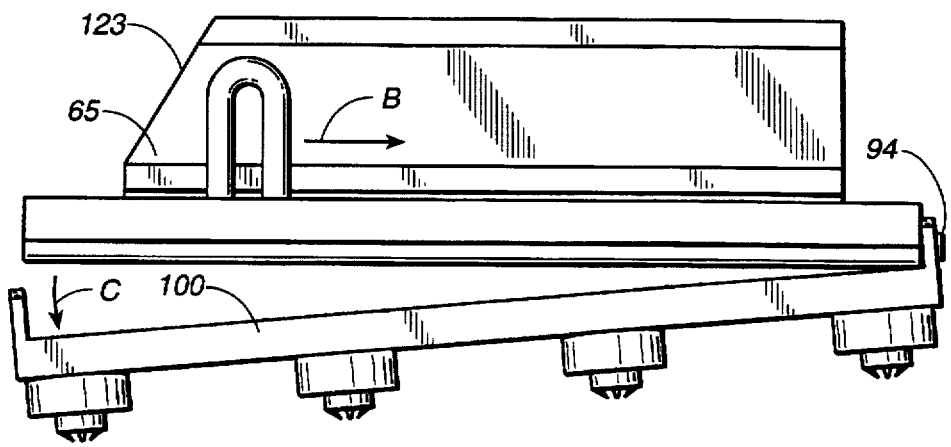
FIG. 15

SKIN TEST APPLICATOR

CROSS-REFERENCE TO RELATED APPLICATION

This is a continuation-in-part of application Ser. No. 08/086,929, filed Jul. 2, 1993, now abandoned.

BACKGROUND OF THE INVENTION

The present invention relates to devices for performing skin tests for an allergic response or for other diagnostic responses; it more particularly relates to an improved skin test applicator system which can be efficiently stored and which has reusable parts.

Skin tests are a widely used diagnostic tool for clinical allergy evaluations and, indeed, is a standard clinical method for demonstrating whether or not the patient has allergen-specific antibodies associated with allergic disease. The skin test generally involves applying a drop of a desired allergenic extract to the skin by either prick or puncture technique using a skin testing device.

One well-known approach to skin testing is to simultaneously apply different antigens to multiple sites on the skin. Such multiple skin tests are widely performed by a skin test applicator disclosed in U.S. Pat. No. 3,556,080 to Gary L. Hein, which discloses a plastic applicator consisting of a plurality of multiple pressure puncture heads integrally connected by relatively flexible arms to a relatively rigid handle. The entire applicator of the Hein patent is intended to be disposable due to the sterile requirements for skin testing.

The unitary skin test applicator disclosed in U.S. Pat. No. 3,556,080 has a number of disadvantages. First, a single use of the applicator exhausts the entire applicator, including the handle, which must be thrown away, whereas the only non-sterile parts of concern on the applicator are the pressure heads and skin puncturing scarifying points on the applicator. Secondly, the applicator is relatively bulky requiring shipment and storage in a sealed, bacteriostatic, individualized container which itself is relatively bulky. Therefore, where adequate storage space is not available, stocking large quantities of these applicators as is normally required by an allergist, can be an on-going problem.

Another problem discovered with the skin test applicator disclosed in U.S. Pat. No. 3,556,080 is that the diagnostic accuracy of the applicator tends to be relatively low. It is believed this is due to the relative close spacing of the test heads (20 mm). Therefore, a need exists for a multiple skin test applicator having greater spacing between test heads.

The present invention overcomes the disadvantages of the unitary applicator disclosed in U.S. Pat. No. 3,556,080 by providing a multiple test applicator wherein the test elements carrying the spaced-apart skin puncturing pressure heads are separately storable elements and are the only portion of the applicator that are intended to be disposable. The invention also provides a multiple skin test applicator that will tend to reduce problems of diagnostic accuracy associated with test sites spaced too closely together.

SUMMARY OF THE INVENTION

Briefly, the invention provides for a skin test applicator having an applicator handle and separately storable applicator test elements, each of which has at least one, and preferably three to four, skin puncturing test pressure heads for holding a desired allergenic agent. Complimentary coupling means are provided on the test elements and applicator handle to permit the handle to operatively pick up and hold the test elements when they are used. It is contemplated that the separately storable applicator test elements will be packaged in easily storable, sterile trays with their coupling means facing up to receive the complimentary coupling means of the applicator handle. The test elements can thus be picked up by the applicator handle without touching the technician's skin.

Preferably, the handle of the skin test applicator will be capable of picking up at least two applicator test elements. Thus, for example, if the applicator handle picks up two test elements, each having four pressure heads, each administration of the skin test with the test applicator of the invention can accomplish eight different skin tests at eight different sites on the skin.

The complimentary coupling means on the applicator handle and the storable test elements are preferably comprised of complimentary snap-fit attachment means, wherein the applicator handle operatively engages and holds the test elements when the snap-fit attachment means on the applicator handle is pressed into snap-fit engagement with the complimentary snap-fit attachment means on the test elements held in an open storage tray.

In one illustrated embodiment, the snap-fit attachment means are comprised of snap-fit channel means that will permit the test elements to be slidably removed from the applicator handle when a skin test is complete. Such channel means can include open-ended receiving channels on the applicator handle and corresponding channel locking means, such as spaced apart, inwardly depressible locking tabs projecting from the test element. The locking tabs can be lockingly engaged into the receiving channel when the receiving channel of the applicator handle is forced against the locking tabs. It is understood that this construction could be reversed, that is, the test elements could be provided with receiving channels and the applicator handle provided with extending locking tabs, or other depressible channel locking means.

In another illustrated embodiment of the invention, the snap-fit attachment means includes a hand-operable release means for releasing the test elements by a simple motion of the user's finger while holding the applicator handle. Preferably, the release means includes a latch mechanism on the applicator handle itself which releasably engages the test elements. Suitably, the latch mechanism includes at least one latch pin which retractably snaps into snap-fit latch pin receiving means on the test elements whereby the latch mechanism can be actuated to retract the latch pin to release the test elements from the applicator handle without the need to push or pull or otherwise touch the applicator handle.

While the test elements described below are in the form of straight, elongated test strips, it will be readily appreciated that the test elements might take on numerous shapes, for example, round, square, or curvilinear test elements. However, straight elongated test strips are the contemplated best mode of the invention, since they are easily removable, as hereinafter described, and best provide for adequate spacing between test pressure heads.

In a further aspect of the invention, the pressure heads on the applicator test strips are alternatingly disposed on opposite edges of the test strip to provide a staggered pattern of test heads. Such a staggered pattern will provide a greater spacing between the skin test sites as compared to the same number of test heads being aligned on the test strip. The greater spacing between test sites on the skin will improve accuracy and interpretation of each test site on the skin.

3

Therefore, it can be seen that it is a primary object of the invention to provide a skin test applicator that reduces storage requirements by permitting the sterile test elements of the applicator to be stored apart from the relatively bulky handle of the applicator. It is a further object of the invention to provide a skin test applicator that is easy to use and that has less total plastic to discard when the skin test is complete, thereby reducing costs and producing less refuse materials for disposal. It is still a further object of the invention to provide a multiple skin test applicator that has improved accuracy by providing for increased spacing between test sites on the skin. Other objects of the invention will be apparent from the following specification and claims.

DESCRIPTION OF THE DRAWINGS

FIG. 1 is an exploded perspective view of a skin test applicator in accordance with the invention showing two test elements in a snap-fit orientation with the applicator handle and a storage tray for the separately storable test strips.

FIG. 2 is a perspective view of the skin test applicator of the invention showing the test strips in snap-fit engagement with the applicator handle.

FIG. 3 is a side elevation, cross-sectional view of the skin test applicator of FIG. 2.

FIG. 4 is a side elevational view of the skin test applicator of FIG. 2 showing the test strips being removed from the applicator handle.

FIG. 5 is a bottom plan view of a test strip for a skin test applicator in accordance with the invention showing a staggered arrangement of pressure heads on the test strip.

FIG. 6 is an alternative embodiment of a test strip for a skin test applicator in accordance with the invention showing the pressure heads aligned on the test strip.

FIG. 7 is a bottom plan view of the applicator handle shown in FIGS. 1–4.

FIG. 8 is a top perspective view of an alternative embodiment of the invention having a hand-operable test strip release mechanism on the applicator handle.

FIG. 9 is an exploded top perspective view thereof showing the test strips separated from the applicator handle.

FIG. 10 is an exploded top perspective view thereof showing the assembly of the different parts of the applicator handle.

FIG. 11 is an end elevational view thereof.

FIG. 12 is a cross-sectional end elevational view thereof taken along lines 12—12 of FIG. 8.

FIG. 13 is a right-side elevational view thereof showing the test strips in a position to be picked up by the applicator handle.

FIG. 14 is a right-side elevational view thereof showing the test strips engaged to the applicator handle.

FIG. 15 is a right-side elevational view thereof showing the test strips being released from the applicator handle.

DETAILED DESCRIPTION OF THE ILLUSTRATED EMBODIMENT

Referring now to the drawings, FIG. 1 shows a skin test applicator 11 in accordance with the invention wherein test elements, which are in the form of elongated test strips 13 having a plurality of pressure heads 15 for contacting and puncturing the skin, are separately storable in a storage tray 17. As shown in FIG. 1, the test strips 13 are deposited in channels 19 formed in the bottom of the storage tray and are adapted to be picked up from the tray by an applicator handle 21. The tray, which is relatively shallow and stackable for easy and compact storage, can be fabricated of thermoformed plastic. Its perimeter is provided with a shoulder surface 23 of sufficient width to receive a sterile peel-off cover such as a Tyvek® cover 22 manufactured by The DuPont Corporation. While, in FIG. 1, the tray is shown as holding four test strips, it is understood that the tray can be designed to hold any number of test strips as required. Also, as shown in FIG. 1, the tray can be designed to have two or more compartments 26, 28, with each compartment containing multiple test strips and covered by a separately removable Tyvek cover or the like. By providing a relatively small tray, or trays with relatively small compartments, only a few sterile test strips need be exposed at a time when a skin test is performed. This will reduce waste in the event all of the test strips are not used.

Each of the skin test strips 13 and the applicator handle 21 have complimentary coupling means to permit the handle to operatively pick up and hold skin test strips when a skin test is performed. In the illustrated embodiment, the coupling means on the applicator handle provide the handle with the ability to pick up and hold the two test strips at the same time. It shall be appreciated that the coupling means on the applicator handle could as well provide for picking up just one test strip or more than two test strips, however, the facility for picking up two test strips is best suited for skin testing and is the contemplated best mode of the invention.

The applicator handle 21 is more specifically seen to include laterally extending side portions 24, 25 and a vertically extending gripping portion 27 having a notch 30 which is useful for registering the applicator handle in a holding tray (not shown) as described below. The laterally extending side portions which have top surfaces 29 also create a bottom surface 31 on which the test strips are retained. The applicator handle more specifically includes a row of relatively short, open-ended receiving channels 33 arranged along each lateral side edge 35, 37 of the handle's bottom surface 31. These channels provide the handle's coupling means and hold two test strips in parallel spaced relation on the handle. Except for the notch 30 and cut-away portions 36 which create the short channel sections 33, the handle, including the lateral side portions, gripping portion, and receiving channels have an uniform cross-section such that the entire applicator handle can be fabricated from extrudable or injection molded plastic. It shall be appreciated that the receiving channels could be continuous channels, instead of relatively short machined channel sections; however, the relatively short channels illustrated in the drawings have the advantage that they permit the test strips to be more easily removed from the application handle as still further described below.

Each of the illustrated test strips 13 is comprised of an elongated, relatively narrow base member 39 terminated at each end by upward extending push/pull tabs 41. The complimentary coupling means on the test strip is in the form of depressible channel locking means consisting of pairs of substantially parallel, inwardly depressible locking tabs 43 that project from the lateral edges 45, 47 of base member 39 in a spaced apart relation that corresponds with the width of the receiving channels 33 on the bottom surface 31 of the applicator handle.

Each pair of locking tabs on the test strips have projecting locking ends 49 that snap-fit into the receiving channels when the ends of the locking tabs are forced against the channel. Specifically, with reference to FIG. 3, it can be seen that the ends of the locking tabs have an outwardly projecting rib structure 51, which includes a forward angled surface 53 that fits into a corresponding lateral recessed area 55 in the side walls of the locking channel. As the forward angled surfaces 53 press against the forward angled surfaces 57, the locking tabs will be depressed inwardly to snap into the locking channels. It will be appreciated that the locking tab arrangement shown in FIGS. 1–7 could be molded so that, for example, the depressible locking tabs are made to project from the applicator handle with the locking channels being formed on the test strip, or the locking tabs could be made to snap-fit over the outside of the channel walls by providing for an inwardly facing locking rib structure and an outwardly facing corresponding recess formed in the outside of the channel side walls.

The pressure heads 15 on the test strips 13 each carries a plurality of scarifying points 61 that hold an allergenic extract. The scarifying points puncture the skin with the allergenic extract when the heads are pressed against the skin, causing test reactions at multiple adjacent sites on the skin.

FIGS. 5 and 6 show two different arrangements of pressure heads on the test strips. In FIG. 6 three pressure heads 15a are provided that are aligned in the center of the base member 39a of test strip 13a, whereas in FIG. 5 four pressure heads 15b are provided which are alternatingly attached to opposite lateral edges of base member 39b. The advantageous increase in the number of pressure heads in the FIG. 5 embodiment would normally result in a disadvantageous decrease in the distance between pressure heads, given a set length for the test strips. However, this disadvantage is mitigated by the increase in distance between pressure heads that occurs because of the staggered arrangement of the heads. As above-mentioned, the spacing of the pressure heads on the test strip is important because pressure heads that are too closely spaced together may produce false-positive reactions by allowing one skin test reaction to affect an adjacent testing site.

The use of the skin test applicator of the invention is best illustrated with reference to FIG. 1. To use the applicator, a tray 17 of sterile test strips 13 is removed from storage and the tray opened to expose the test strips which are arranged in the tray with their snap-fit attachment means facing up. By holding an applicator handle 21 by its gripping portion 27, the person preparing for a skin test simply presses the receiving channels 33 located on the underside of the applicator handle (bottom surface 31) against the depressible locking tabs 43 of two alternate test elements 13 in the tray until the locking tabs snap into place in the receiving channels. For this purpose, the tray should be placed on a level, horizontal surface. The applicator handle and attached test elements are then removed to a separate holding tray (not shown) where, in a manner well-known in the art, they are held in an inverted position for the purpose of preparing the applicator, that is, for the purpose of applying different allergenic agents to the scarifying points 61 of the different pressure heads. The notch 30 on the gripping portion of the handle can be utilized with a corresponding hump molded into the holding tray to register the handle at a desired orientation within the tray.

Since each pressure head will be prepared with a different allergenic agent, it is necessary to keep track of which agent is applied to which pressure head. For this purpose, the top surfaces 29 of lateral side portions 24, 25 of the applicator handle provide a ready structure for imprinting indicia 32 on the underside of the handle for identifying each pressure head when the applicator is prepared for use. Because of the broad surfaces provided, the indicia can be large enough to be easily read for quick identification.

Once the first two sterile test strips have been picked up in the tray as shown in FIG. 1, the remaining two skin test strips can be picked up by a separate applicator handle. It is contemplated that a number of handles would be provided such that a number of test applicators can be prepared at the same time.

Allergy testing of a patient may call for up to sixty or more skin tests. If, for example, skin testing is performed on a patient requiring sixty different allergenic agents, fifteen test strips having four pressure heads as shown in FIG. 5, or twenty test strips having three pressure heads as shown in FIG. 6, would be required. If an odd number of test strips is required, only one test element need be picked up by an applicator handle for the final test series, thereby conserving test strips. This is accomplished by pressing one side of the handle onto a test strip in tray 17 in order to releasably lock on that specific test strip.

Once the skin tests are performed, the test strips illustrated in FIGS. 1–7 can be easily removed from the applicator handle by simply pushing or pulling on the push/pull tabs 41 of the test strips to slide the test strips from the handle's open-ended receiving channels 33. For example, after administering a test, the test administrator need only knock the applicator against a table such that the tabs of the test strips hit the table's edge. This simple motion dislodges the test strips from the handle, preferably into a receptacle for disposal suitably placed below the table top. This is done without the need to manually touch the strips. Thus, it can be seen that the skin test applicator of the invention can be used in a way that the separately storable test elements are not manually touched at any time from retrieval to discard. It can also be seen that because only the test elements of the applicator are discarded, instead of the entire applicator, and because the sterile tray holding the test elements is smaller than would be required if an entire applicator handle and test elements were stored in a sterile tray, there is less overall plastic material that needs to be discarded.

FIGS. 8–15 illustrate an alternative embodiment of the invention having an easily operable finger-actuated means for releasing the test strips from the applicator handle after the test strips have been used for a skin test. In this embodiment, the test strips can be released without the need to push or pull on the test strips directly, or to otherwise touch the test strips. The construction of the applicator handle illustrated in FIGS. 8–15 is a multi-part stacked construction involving easy to assemble, and suitably injection molded, plastic parts.

As best illustrated in FIGS. 8–12, the handle 63 of skin test applicator 60 is comprised of grip portion 65, as well as a base plate 67 and bottom cover plate 69 which provide the handle with laterally extending side portions 62, 64 to which test strips 100 can be attached in a suitable spaced relation; the handle also comprises means for releasing the test strips from the applicator handle in the form of a latch mechanism (which includes latch pins 73, bias springs 75, and stationary pins 77) and a finger depressible slide member 71 linked to the latch mechanism. Referring to the exploded view of FIG. 10, it can be seen that the extended flat bottom portion 79 of grip portion 65 fits within recess 81 formed in the top of base plate 67, and that the bottom cover plate 69 fits over the underside of the base plate in order to hold the handle's latch mechanism—that is, pins 73, 77 and springs 75—in the latch grooves 83 formed along the base plate's bottom lateral edges 85. During assembly, the grip portion 65, base plate 67, and bottom cover plate 69 can suitably be jointed together using ultrasonic welding techniques.

More specifically, each of the movable latch pins 73 of the latch mechanism is seen to consist of a bent metal pin having a diameter that permits the straight portions 87 of the pins to slide within the latch grooves 83. The bend in the latch pins form riser portions 89 that operatively project through elongated latch pin openings 91 that extend through the edges of the base plate in registration with the latch grooves. The stationary pins 77, on the other hand, are straight pins that are non-movably secured within the latch grooves at the end of the applicator handle opposite the movable latch pins. The stationary pins can be glued in place, or alternatively, or in addition to gluing, they can be provided with an interior flatten or flared end (not shown) which is captured within a corresponding slot or flared portion molding into the latch grooves. Springs 75, which fit in the latch grooves between the stationary and movable pins, bias the movable pins in a forward extended position so that the ends 93 of the movable pins extend beyond the front edge 95 of the applicator handle to engage the test strips as hereinafter described.

As best seen in FIGS. 10–12, bottom cover plate 69 is shaped to mate with the bottom of the base plate 67. Channels 97 formed along the top lateral edges of the cover plate form a cap for covering the base plate's bottom lateral edges 85 and the parts of the latch mechanism. Bracing ridges 99 formed on the underside of the cover plate's lateral edges are provided to fit within and engage the test strips' channel walls 101 when the test strips are picked up by the applicator handle. These ridges will act to keep the test strips from rocking on the applicator handle when the test strips are pressed against a patient's skin.

Referring to FIG. 10, the applicator handle is assembled by securing the grip portion 65 within the recess 81 of the base plate while fitting slide 71 onto the front of the base plate such that the guide slot 103 formed in the slide fits over the grip's vertical wall 105 between the grip's flat bottom portion 79 and guide ridges 80. With the slide's linkage arms 107 positioned over the latch pin openings 91 of the base plate (and before positioning the bottom cover plate over the bottom of the base plate), the pins and springs of the latch mechanism are positioned in the latch grooves. In position, the riser portions 89 of the movable latch pins will project through latch pin openings 91 so as to engage the openings 109 in the slide member's linkage arms.

As noted above, the stationary pins can be secured in place by means of a flat or flared end. A flat end can easily be provided on the stationary pins by striking the end of the pins with a hammer or weighted object before installing the pin. It is also noted that a flat bottom portion 79 of grip 65 is provided with dovetailed edges, the bottom portion of which mates with chamfered edges 84 of the base plate's recess 81. Dovetailing the edges in this manner will increase the strength of the joint between the grip and the base plate.

When assembled, slide 71 will slidably be captured between the top of the base plate 67 and the guide ridges 80 of grip portion 65; also the maximum forward biased position of the slide will be reached when the latch pin riser portions 89, which link the slide to the latch mechanism, strike the forward edge of latch pin openings 91. To minimize the sliding friction between the slide and the base plate, interior top surface portions 111 are recessed relative to other surrounding surfaces of the base plate. Thus, it can be seen that the slide only contacts the base plate along interior ridges 113 and the centered raised portion 115. The base plate's perimeter shoulders 117 act as vertical guide walls for the linkage arms of the slide. By supporting and containing the slide member in this manner, any tendency of the slide to bend or cock about a vertical or horizontal axis will be adverted.

The skin test applicator of FIGS. 8–15 is used to pick up pairs of elongated sterile test strips 100 from a sterile storage tray (not shown) in much the same manner as described in connection with the embodiment of the invention illustrated in FIGS. 1–7. In this case, the complimentary coupling means on the applicator handle and test strips is a snap-fit attachment means comprised of the latch mechanism associated with the handle and snap-fit latch pin receiving means on the test strips which are in the form of upward extending expandable pairs of locking arms 119 at the opposed ends of the test strips. More specifically, the pairs of test strip locking arms are designed to snap into engagement with the ends 93, 94 of the movable and stationary pins that project beyond the front and rear edges 95, 96 of the applicator handle.

Referring to FIGS. 9 and 13–15, it can be seen that a pair of test strips 100 having staggered pressure heads 102, are picked up by applicator handle 63 by first aligning the projecting ends 93, 94 of the handle's movable and stationary pins over test strip locking arm pairs 119, and then pressing the handle down against the test strips (as indicated by arrows A in of FIG. 13) until the projecting ends of the pins snap into place as shown in FIG. 14. (As in the earlier described embodiment, each of the pressure heads 102 should be numbered to make it easier to keep track of the allergenic agents applied thereto. Numbers or other identifying indicia (not shown) can readily be imprinted on the underside of the bottom cover plate 69.) After using the applicator, the test strips 100 are released manually by simply pushing on the extended end 121 of slide member 71 at the front edge 95 of the applicator handle while holding the grip 65 of the handle. This release action can suitably be accomplished by extending the index finger to press the slide. To facilitate the extension of the index finger over the front of the applicator grip, the grip is preferably provided with an angled front edge 123. The simple motion of pushing inwardly on the slide will cause the movable latch pin to retract, as indicated by arrow B in FIG. 15, resulting in the test strips 100 separating from the handle, in this case indicated by arrow C in FIG. 15. The applicator handle can be tilted front end up when the test strips are released to prevent the back end of the test strips from hanging up on the stationary pin.

As in the case of the earlier described embodiment of the invention, the test strips are preferably released from the applicator handle directly into a receptacle for suitable disposal. Also as previously mentioned, only the test strips will be discarded rather than the entire applicator, such that the applicator can be reused. Furthermore, the entire skin test procedure, including picking up and discard of the test strips, can be accomplished without any contact between the user's hand and the sterile test strips.

It will be appreciated that the finger actuated test strip release means on the applicator handle, and the latch mechanism therefor, can be implemented in a variety of ways other than illustrated in FIGS. 8–15, including using a member that depresses rather than slides for actuating a complimentary latch mechanism that releases the test strips. However, the illustrated embodiment (FIGS. 8–15) is considered to be the best mode of the invention in that it is believed to combine both simplicity and reliability of operation with ease and low cost of manufacture and assembly as compared to other latch design approaches.

Therefore, the present invention provides for a skin test applicator that is easy to use, that reduces storage requirements, and that generates less waste for disposal. The invention also provides test elements that have pressure heads suitably spaced to reduce the risk of false-positive readings. Also, only the number of test elements required for a particular skin test procedure need be used by the administrator of the skin test. While the invention has been described in considerable detail in the foregoing specification, it shall be understood that it is not intended that the invention be limited to such detail, except as necessitated by the following claims.

We claim:

1. A skin test applicator comprising
   an applicator handle,
   a plurality of elongated test strips storable separately from said applicator handle, each of said test strips having a plurality of skin-puncturing test heads, said test heads being disposed in spaced relation on each of said test strips for receiving and holding desired testing agents for producing simultaneously applied and spaced apart diagnostic skin tests when said test strips are pressed against a skin surface,
   at least one of said test strips having test heads alternatingly disposed on opposite edges thereof to provide a staggered pattern of test heads, and
   complimentary coupling means on each of said test strips and on said applicator handle to permit said handle to operatively pick up and hold any one of said test strips when said test strips are used.

2. A skin test applicator comprising
   at least one separately storable applicator test element having at least one skin-puncturing test head for holding a desired testing agent for a diagnostic skin test when said test element is pressed against a skin surface,
   an applicator handle, and
   complimentary coupling means on said test element and said applicator handle to permit said handle to operatively pick up and hold said test element when it is desired to use said test element, said complimentary coupling means including finger actuated test element release means on said applicator handle for releasing test element picked up and held thereby.

3. The skin test applicator of claim 2 wherein said test element release means provides means for snap-fit attachment of the test element to said applicator handle.

4. The skin test applicator of claim 2 wherein said test element release means includes a retractable latch mechanism on said applicator handle and latch receiving means on said test element.

5. The skin test applicator of claim 4 wherein said latch receiving means is a snap-fit latch pin receiving means, and said latch mechanism includes at least one retractable latch pin extending from said applicator handle for retractably snapping into the snap-fit latch pin receiving means on said test element.

6. The skin test applicator of claim 5 wherein the snap-fit latch pin receiving means on said test element is comprised of at least one pair of upwardly extending expandable pair of locking arms on said test element for receiving the retractable latch pin of the latch mechanism on said applicator handle in a snap-fit engagement.

7. The skin test applicator of claim 2 wherein said applicator handle has a front edge and a grip portion, and wherein said test element release means is actuated by a finger of a hand holding the grip portion at the front edge of the applicator handle.

8. The skin test applicator of claim 7 wherein the grip portion of said applicator handle has an angled front edge to facilitate the extension of the finger thereover.

9. A skin test applicator handle for operatively holding skin test elements storable separately therefrom comprising
   a grip portion,
   laterally extending side portions, and
   test element coupling means for releasably coupling to complimentary coupling means on the storable skin test elements to permit said applicator handle to operatively pick up and releasably hold the test elements in spaced relation along the lateral side portions thereof,
   the test element coupling means on said applicator handle providing means for snap-fit attachment of said skin test elements to the applicator handle and including a retractable latch mechanism for retractably engaging latch receiving means on the separately storable skin test elements.

10. A skin test applicator handle for operatively holding skin test elements storable separately therefrom comprising
    a grip portion,
    laterally extending side portions, and
    test element coupling means actuated at the front edge of the applicator handle by a finger of a hand holding the grip portion thereof to releasably couple to complimentary coupling means on the separately storable skin test elements to permit the applicator handle to operatively pick up and releasably hold the test elements in spaced relation along the laterally extending side portions thereof.

11. The skin test applicator handle of claim 10 wherein said grip portion has an angled front edge to facilitate the extension of the finger thereover.

12. The applicator handle of claim 10 wherein said latch mechanism includes latch grooves disposed in the laterally extending side portions of the handle, spring biased latch pins retractably extending beyond said handle for engaging latch pin receiving means on separately storable skin test elements, and a finger actuated slide member linked to said latch pins and located at the front edge of the handle.

13. A skin test applicator handle for releasably picking up and holding separately storable skin test strips having a pair of upwardly extending expandable pair of locking arms on each end thereof, said applicator handle comprising
    a base plate having a top, a bottom, lateral side edges, a front defining the front edge of the applicator handle, a rear defining the rear edge of the applicator handle, a latch groove extending along each of the lateral edges thereof, and latch pin openings extending through the base plate in registration with said latch grooves,
    a grip portion on the top of said base plate,
    stationary pins having ends that project from the rear edge of the applicator handle,
    a spring biased latch pin movably disposed in each of the latch grooves of said base plate so as to have ends that retractably project beyond the front edge of the applicator handle, said latch pins having riser portions extending through the latch pin openings in said base plate,
    the projecting ends of said movable latch pins and stationary pins acting to snap into the expandable pairs of locking arms at the ends of the skin test strips for holding the test strips to the applicator handle, and
    a finger accessible slide member slidably engaged to the top of said base plate, said slide member being linked to the riser portions of said latch pins so that moving said slide member retracts the projecting ends of the movable latch pins to release the latch pins from the locking arm pairs of the test strips to which they are engaged to thereby release the test strips from the applicator handle.

* * * * *